United States Patent
Stevens et al.

(10) Patent No.: US 6,534,647 B1
(45) Date of Patent: Mar. 18, 2003

(54) SURFACE-ACTIVE ALKYLURETHANES OF FRUCTANS

(75) Inventors: Christian Victor Stevens, Merelbeke-Schelderode (BE); Karl Booten, Geetbets (BE); Isabelle M.-A. Laquiere, Ghent (BE); Lucien Daenekindt, Gijzegem-Aalst (BE)

(73) Assignee: Tiense Suikerraffinaderij N.V. (BE)

( * ) Notice: Subject to any disclaimer, the term of this patent is extended or adjusted under 35 U.S.C. 154(b) by 0 days.

(21) Appl. No.: 09/719,321

(22) PCT Filed: Jun. 8, 1999

(86) PCT No.: PCT/EP99/03931
§ 371 (c)(1),
(2), (4) Date: Dec. 11, 2000

(87) PCT Pub. No.: WO99/64549
PCT Pub. Date: Dec. 16, 1999

(30) Foreign Application Priority Data

Jun. 11, 1998 (EP) ............................................. 98870135

(51) Int. Cl.$^7$ ............................................... C07H 11/00
(52) U.S. Cl. ............... 536/115; 536/123.1; 536/123.12; 536/124
(58) Field of Search ............................. 536/115, 123.1, 536/123.12, 124

(56) References Cited

U.S. PATENT DOCUMENTS 5,223,411 A * 6/1993 Plusquellec et al. ........ 435/71.2

FOREIGN PATENT DOCUMENTS

| EP | 0792888 | 9/1997 | ........... C08B/37/18 |
| EP | 0821885 | 2/1998 | ........... A23L/1/308 |
| JP | 002085198 | 12/1992 | ........... C11D/10/04 |
| NL | WO 96/34017 A1 * | 10/1996 | |
| WO | WO 96/34017 | 10/1996 | ........... C08B/37/00 |

* cited by examiner

Primary Examiner—Dwayne C. Jones
(74) Attorney, Agent, or Firm—Hayes Soloway P.C.

(57) ABSTRACT

The invention concerns the use as surface-active agent of a fructan N-alkylurethane (I) which is composed of saccharide units of general formula (II)

$$A(O\text{—}CO\text{—}NH\text{—}R)_s \quad (II)$$

wherein

A represents a fructosyl unit (F) or a terminal glucosyl unit (G) of said fructan, being a levan or an inulin, with a degree of polymerisation (DP) of minimum 3, (O—CO—NH—R) represents an N-alkylaminocarbonyloxy group replacing a hydroxyl group of the saccharide unit A, wherein R represents a linear or branched, saturated or unsaturated alkyl group containing from 3 to 22 carbon atoms and any mixture thereof, and s represents the number of N-alkylaminocarbonyloxy groups per saccharide unit which is expressed as degree of substitution (DS), and said DS has a value ranging from 0.10 to 2.0. The invention further relates to novel fructan N-alkylurethanes (I), in particular inulin N-alkylurethanes (I), and a method for their manufacture. The fructan N-alkylurethanes (I) have good to excellent surface-active properties in combination with good biodegradability and are suitable as surfactants for use in household and industrial applications, e.g. as detergents, emulsifiers, emulsion stabilizers, foaming agents, foam stabilisers, dispersants and wetting agents.

11 Claims, 3 Drawing Sheets

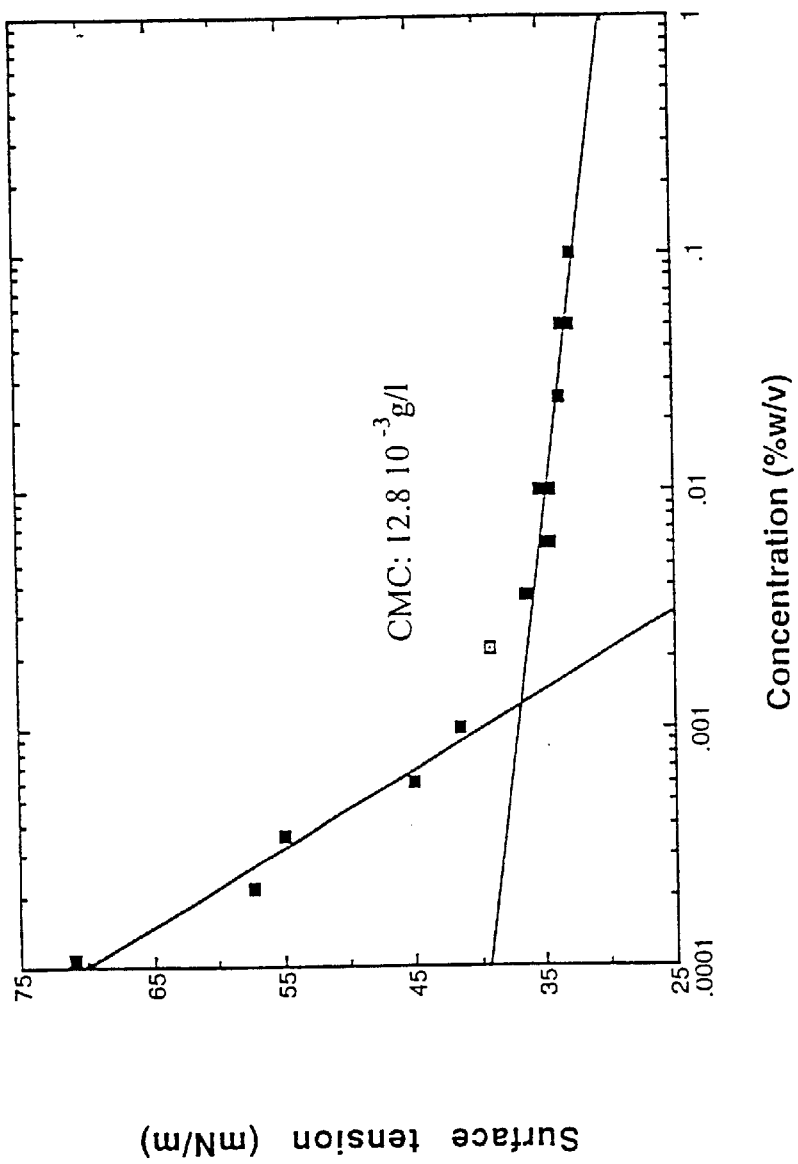
Fig 1: Determination of critical micelle concentration (CMC) in water of inulin ($\overline{DP}$:25) N-n-octylcarbamate ($\overline{DS}$:0.56) (18)

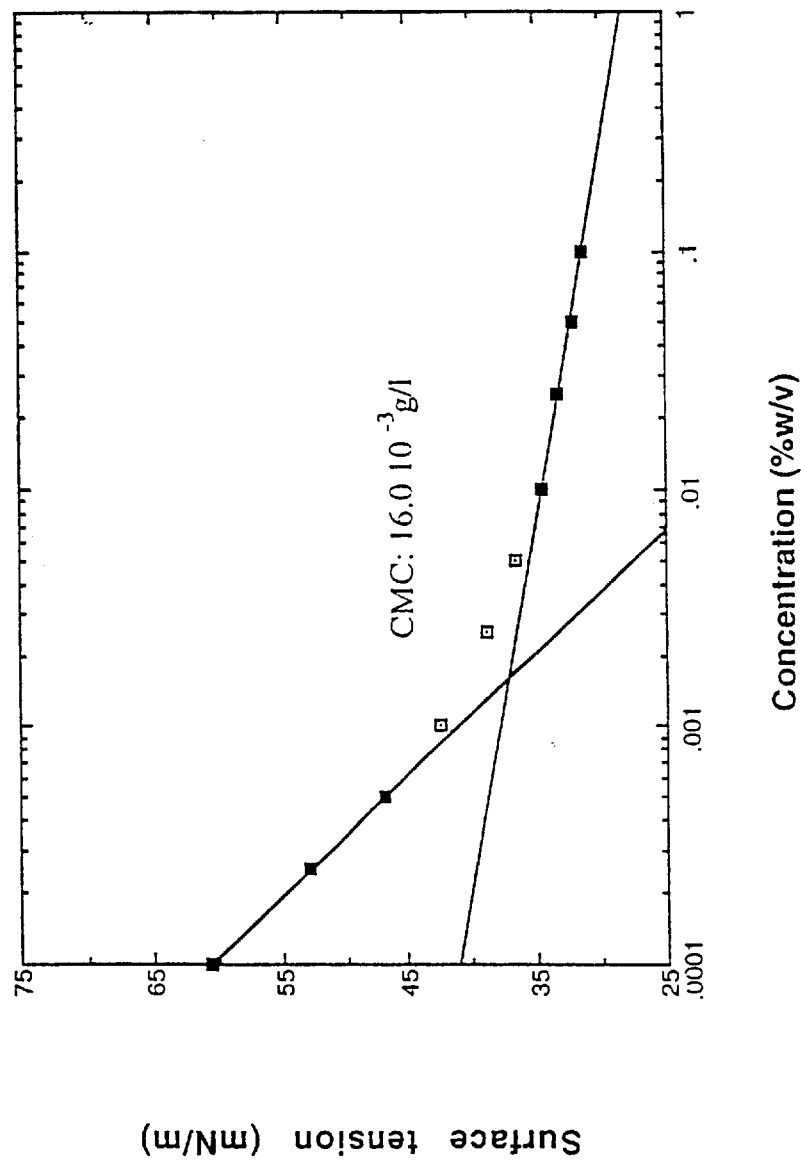
Fig 2: Determination of critical micelle concentration (CMC) in water of inulin ($\overline{DP}$:10) N-n-octylcarbamate ($\overline{DS}$:0.53) (20)

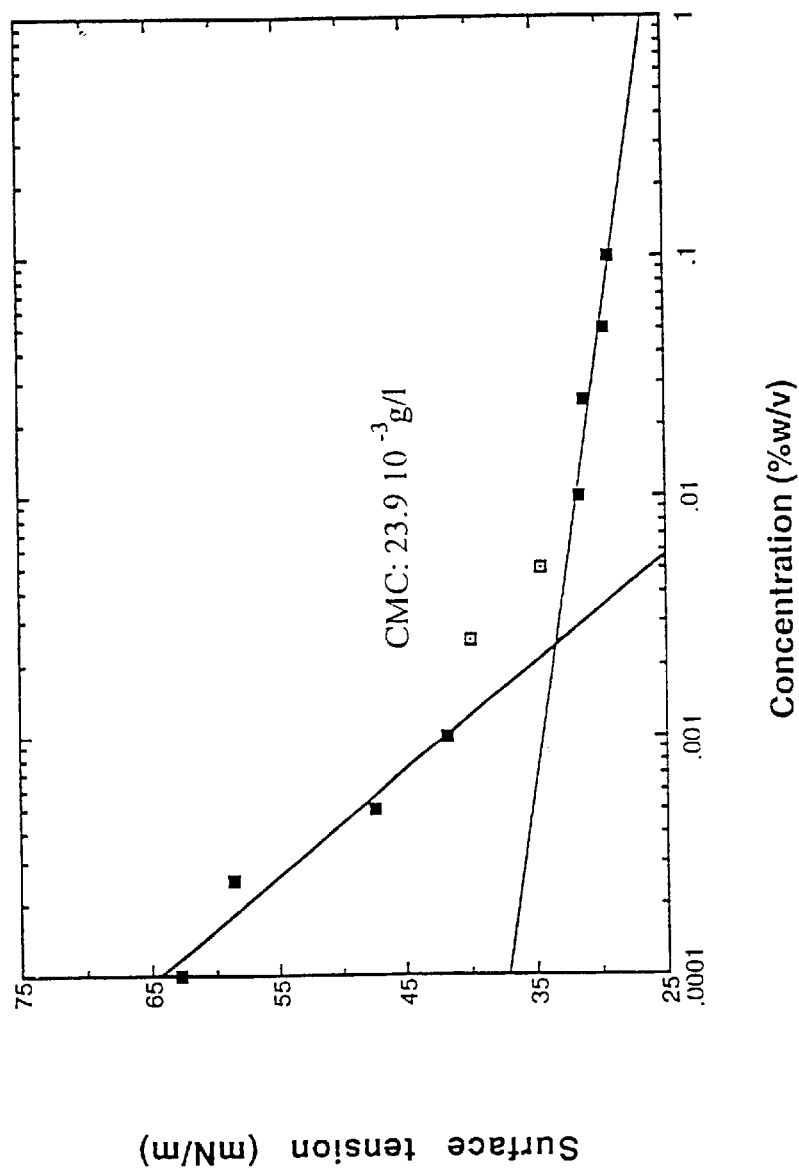
Fig 3: Determination of critical micelle concentration (CMC) in water of inulin (95% DP:2-7) N-n-octylcarbamate (DS:0.51) (21)

SURFACE-ACTIVE ALKYLURETHANES OF FRUCTANS

This application is a 371 of PCT/EP99/03931, filed on Jun. 5, 1999.

FIELD OF THE INVENTION

This invention relates to the use of alkylurethanes of fructans as surfactants, to compositions comprising alkylurethanes of fructans as surfactants, to novel alkylurethanes of fructans and to a process for their manufacture.

BACKGROUND AND PRIOR ART

Surface-active agents are widely used in compositions for household and industrial applications in which they act as detergents, foaming agents, foam stabilisers, wetting agents, emulsifiers and/or emulsion stabilisers. The oldest type of surface-active agents, mainly used as detergents, are the alkali soaps of fatty acids. Later on these soaps have been replaced to a large extent by much stronger synthetic surfactants. The elder generation of synthetic surfactants consisted mainly of alkylbenzenesulfonates (ABS). However, ABS caused considerable water pollution due to their poor biodegradability. At present, ABS have been largely replaced by linear alkylsulfonates (LAS) having ten or more carbon atoms in the alkyl chain, which present improved biodegradability compared to ABS surfactants.

To day, the search for alternative, more efficient and better biodegradable surfactants is still going on.

According to one approach, sugars such as glucose and sucrose (saccharose) have been used as starting material for the synthesis of non-ionic derivatives with surface-active properties.

V. Maunier et al. (Carbohydrate Research, 299, 49–57, (1997)) disclosed tensio-active properties of several 6-aminocarbonyl derivatives of methyl α-D-glucopyranoside and D-glucose and compared them with the ones of the urethane named methyl 6-O-(N-heptylcarbamoyl)-α-D-glucopyranoside.

T. Lesiak et al. (J. prakt. Chem., 322 (6), 877–883, (1980)) disclosed the use of 1-methyl-2,4-bis(isocyanato)benzene (commonly named tolylene-2,4-diisocyanate; in short 2,4-TDI) for the synthesis of urethanes of glucose and sucrose. First 2,4-TDI was reacted with various aliphatic long chain alcohols or terpene alcohols in a molar ratio 1:1. The reaction essentially occurred with the isocyanate group at position 4 and the urethane-mono-isocyanates obtained were then reacted with glucose, respectively sucrose, to yield the corresponding di-urethanes which presented moderate tensio-activity.

The synthesis of several sucrose N-n-alkylurethanes and their tensio-active properties have been disclosed inter alia by H. Bertsch et al. (J. prakt. Chem., 11, 108 (1960)) and by W. Gerhardt (Abh. Dtsch. Akad. Wiss. Berlin, Kl. Chem., Geol. Biol., Vol 1966 (6), 24–32, (1967)). These derivatives present moderate to good tensio-active properties but only at rather high concentration. The urethanes have been prepared by reaction of sucrose with the selected n-alkylisocyanate (H. Bertsch et al. o.c.) and by transformation of sucrose with potassium cyanate and an n-alkyl-halogenide in dimethyl formamide (W. Gerhardt, o.c.). However, sucrose n-alkylurethanes with longer alkyl chains, suffer from a moderate to poor solubility in water.

To improve the solubility in water of sugar n-alkylurethanes, corresponding n-alkylurethanes have been prepared from ethoxylated or propoxylated sugars. The synthesis and tensio-active properties of n-alkylurethanes derived from ethoxylated and propoxylated sucrose, respectively mannitol, have been disclosed by W. Gerhardt (o.c. and German Patent DE 1 518 696). Furthermore, 1-(n-alkyloxy)-ethylurethanes of sucrose have been synthesised and their tensio-active properties determined by T. Lesiak et al. (J. prakt. Chem., 319 (5), 727–731, (1977)).

Moreover, the preparation of miscellaneous urethanes derived from various carbohydrates have been disclosed.

European patent application EP 0 801 077 discloses n-alkyl $C_1$–$C_{18}$-urethanes of polysaccharides and ethoxylated polysaccharides, in particular of cellulose, and their use as thermoplastic material. Similarly, German patent application DE 43 38 152 A1 discloses n-alkylurethanes of starch and starch derivatives, such as acetylated starch, and their use as thermoplastic material.

European patent application EP 0 157 365 discloses various urethane derivatives of polysaccharides, inter alia inulin tri(phenylcarbamate), and discloses their use in the optical resolution of racemic mixtures.

I. Wolff et al. (J. Am. Chem. Soc., 76, 757 (1954)) disclosed to have prepared urethanes of starch, but later studies by E. Asveld et al. (Carbohydrate Polymers, 4, 103–110, (1984)) revealed that in the aqueous reaction conditions used by I. Wolff et al. no urethanes but only mixtures of the carbohydrate and the urea compounds have been obtained.

In view of the steadily increasing demand for surface-active agents for use in various applications, industry is continuously confronted with the need for alternative surface-active agents, which preferably present improved tensio-active properties and/or biodegradability.

OBJECT OF THE INVENTION

It is the object of the present invention to provide a solution to one or more of the above mentioned problems by the provision of alternative surface-active products which are readily soluble at low concentration in water at room temperature and which present good tensio-active properties and good biodegradability.

DESCRIPTION OF THE INVENTION

In their search for alternative and/or improved surfactants, the inventors have found that certain urethanes of fructans provide a solution to one or more of said problems.

In accordance with these findings, the present invention provides the use of certain alkylurethanes of fructans as surfactants, certain novel alkylurethanes of fructans suitable for use as surfactants, methods for preparing these compounds, and compositions comprising one or more of said alkylurethanes as surfactants and/or stabilisers.

By surface-active agent, surfactant or tensio-active agent are meant herein compounds that reduce the surface tension when dissolved in water or in an aqueous medium, or which reduce interfacial tension between two liquids, between a liquid and a solid or between a liquid and a gas. These terms are used herein interchangeably. The same applies to the terms designating said properties.

By the term alkylurethanes are commonly indicated a class of compounds resulting from the reaction of an alkylisocyanate with an alcoholic hydroxyl group bearing substrate, whereas the individual reaction products are named as N-alkylcarbamates, i.e. as esters of N-alkylcarbamic acid. However, the terms are often, also in this description, interchanged.

Fructans are well known naturally occurring polysaccharides embracing the carbohydrates levan and inulin.

Levans are D-fructans generally consisting of chains of polyfructose of which the fructose units are connected to each other mostly or exclusively by β(2-6) fructosyl-fructose linkages. Levans occur in nature in certain plant species (in this case they are also called phleins) and also originate from the activity of certain bacteria. Levans can be produced, according to conventional techniques, by extraction from certain plants, by fermentation techniques and by enzymatic in vitro synthesis. Levans usually occur as a polydisperse mixture of said polyfructose chains. The chains may be linear, but mostly they are branched.

Inulins are D-fructans too, generally consisting of chains of polyfructose but of which the fructose units are connected to each other mostly or exclusively by β(2-1) linkages. Inulin occurs in nature, in general, as a polydisperse mixture of polyfructose chains most of which are ending in one glucosyl unit. Inulin can be from bacterial origin, from vegetal origin or can be made in vitro by enzymatic synthesis starting from sucrose. Inulin produced by bacteria is more branched than inulin from plant origin and has commonly a higher molecular weight (ranging from about 2,000 up to about 20,000,000), whereas inulin from plant origin is generally composed of linear or slightly branched polyfructose chains or mixtures thereof with a molecular weight commonly ranging from about 600 to about 20,000.

Inulin can be represented, depending from the terminal carbohydrate unit, by the general formulae $GF_n$ or $F_n$, wherein G represents a glucosyl unit, F a fructosyl unit, and n is an integer representing the number of fructosyl units linked to each other in the carbohydrate chain. The number of saccharide units (fructose and glucose units) in one inulin molecule, i.e. the values n+1 and n in the respective formulae above, are referred to as the degree of polymerisation, represented by (DP). Often, the parameter (number) average degree of polymerisation, represented by $\overline{(DP)}$, is used too, which is the value corresponding to the total number of saccharide units (G and F units) in a given inulin composition divided by the total number of inulin molecules present in said inulin composition, without taking into account the possibly present monosaccharides glucose (G) and fructose (F), and the disaccharide sucrose (GF). The average degree of polymerisation $\overline{(DP)}$ can be determined, for example, by the method described by L. De Leenheer (Starch, 46 (5), 193–196, (1994), and Carbohydrates as Organic Raw Materials, Vol. III, p. 67–92, (1996)).

At industrial scale, inulin is commonly prepared from plant sources, mainly from roots of Chicory (*Cichorium intybus*) and from tubers of Jerusalem artichoke (*Helianthus tuberosus*), in which inulin can be present in concentrations of about 10 to 20% w/w on fresh plant material. Inulin from plant origin is, in general, a polydisperse mixture of linear and slightly branched polysaccharide chains with a degree of polymerisation (DP) ranging from 2 to about 100. In accordance with known techniques, inulin can be readily extracted from said plant parts, purified and optionally fractionated to remove impurities, mono- and disaccharides and undesired oligosaccharides, in order to provide various grades of inulin, as e.g. described in European patent applications EP 0 769 026 and EP 0 670 850.

Inulin is commercially available, typically with a $\overline{(DP)}$ ranging from about 6 to about 40. Inulin from chicory is for example available as RAFTILINE® from ORAFTI, (Tienen, Belgium) in various grades. Typical RAFTILINE® grades include RAFTILINE® ST (with a $\overline{(DP)}$ of about 10 and containing in total up to about 8% by weight glucose, fructose and sucrose), RAFTILINE® LS (with a $\overline{(DP)}$ of about 10 but containing in total less than 1% by weight glucose, fructose and sucrose), and RAFTILINE® HP (with a $\overline{(DP)}$ of at least 23, commonly with a $\overline{(DP)}$ of about 25, and virtually free of glucose, fructose and sucrose).

Inulins with a lower degree of polymerisation, usually defined as a (DP) <10, are commonly named inulo-oligosaccharides, fructo-oligosaccharides or oligofructose. Oligofructose can be conventionally obtained by partial (preferably enzymatic) hydrolysis of inulin and can also be obtained by enzymatic in vitro synthesis from sucrose according to techniques which are well-known in the art. Several grades of oligofructose are commercially available, for example as RAFTILOSE® from ORAFTI, (Tienen, Belgium), e.g. RAFTILOSE® P95 with a mean content of about 95% by weight of oligofructose with a degree of polymerisation (DP) ranging from 2 to 7 and containing about 5% by weight in total of glucose, fructose and sucrose.

In one aspect, the present invention relates to the use as surface-active agent of a fructan alkylurethane (I), also named fructan N-alkylcarbamate (I), which is composed of saccharide units of general formula (II)

$$A(O-CO-NH-R)_s \qquad (II)$$

wherein

A represents a fructosyl unit (F) or a terminal glucosyl unit (G) of said fructan, being a levan or an inulin, with a degree of polymerization (DP) of minimum 3, (O—CO—NH—R) represents an N-alkylaminocarbonyloxy group, also called an alkylcarbamate group, replacing a hydroxyl group of the saccharide unit A, wherein R represents a linear or branched, saturated or unsaturated alkyl group containing from 3 to 22 carbon atoms and any mixture thereof, and s represents the number of alkylcarbamate groups per saccharide unit which is expressed as degree of substitution (commonly abbreviated as DS), i.e. the average number of substituents per saccharide unit of said fructan, and which DS has a value ranging from about 0.10 to about 2.0.

The number of hydroxyl groups per saccharide unit of the fructan molecules which can be substituted by a carbamate group is for a non-terminal, non-branched saccharide unit maximal 3, whereas said number for a terminal saccharide unit and for a non-terminal branched unit is, respectively, 4 and 2. Furthermore, since the DS represents an average number of substituents per saccharide unit, it is obvious that in a fructan N-alkylcarbamate (I) molecule there may be saccharide units present which are not substituted by an alkylcarbamate group at all.

In another aspect, the present invention relates to a composition comprising as surface-active agent one or more fructan alkylurethanes (I) defined above.

In a further aspect, the present invention relates to novel fructan alkylurethanes (I) defined above.

In still a further aspect, the present invention relates to a process for the manufacture of fructan alkylurethanes (I) defined above.

In still another aspect, the present invention relates to a process for the manufacture of compositions comprising as surface active agent one or more fructan alkylurethanes (I) defined above.

In a preferred embodiment of the present invention, the fructan alkylcarbamate (I) is made from a levan. In an other preferred embodiment, the fructan alkylcarbamate (I) is made from an inulin. Levans and inulins which are suitable according to the present invention include, respectively, polydisperse levans and inulins composed of essentially linear polysaccharide chains, of essentially branched polysaccharide chains, as well as of respective mixtures thereof.

In view of its better biodegradability, the inulin is preferably a polydisperse linear inulin or a polydisperse slightly branched inulin or a mixture thereof. When the inulin is a slightly branched one, it is preferably an inulin of which maximally about 3% of the fructose units of the inulin chains present 3 fructosyl-fructose bonds. The degree of branching can be determined by known methods, for example by permethylation techniques in combination with gas chromatography analysis, e.g. as described by L. De Leenheer et al. in Starch, 46(5), 193–196 (1994).

In a more preferred embodiment, said polydisperse inulin consists of polysaccharide chains with a degree of polymerisation (DP) ranging from 3 to 100, typically from about 5 to about 75. Even more preferably said polydisperse inulin has an average degree of polymerisation $(\overline{DP})$ between 6 and 40, most preferably a $(\overline{DP})$ ranging from about 10 to about 35.

The alkyl group of the alkylurethanes (I) of the present invention, i.e. the R group in formula (II), is preferably a saturated alkyl group, more preferably a saturated $C_3$–$C_{18}$ alkyl group, and most preferably a saturated linear or slightly branched $C_6$–$C_{18}$ alkyl group or a mixture thereof. Typically alkyl groups include propyl, butyl, hexyl, octyl, decyl, dodecyl, tetradecyl, hexadecyl and octadecyl, and any mixtures thereof.

In another preferred embodiment, the alkyl group is a mono-unsaturated $C_3$–$C_{18}$ alkyl group, more preferably a mono-unsaturated $C_6$–$C_{18}$ alkyl group, even more preferably a mono-unsaturated $C_6$–$C_{16}$ alkyl group. Typically suitable mono-unsaturated alkyl groups, i.e. alkenyl groups, include hexenyl, octenyl, decenyl, dodecenyl, tetradecenyl, hexadecenyl, octadecenyl, and any mixtures thereof.

In a further embodiment, the alkyl group R can represent a mixture of one or more saturated alkyl groups with one or more unsaturated, preferably mono-unsaturated, alkyl groups.

The alkylurethanes (I) in accordance with the present invention, particularly the ones derived from inulin, have a degree of substitution (DS) preferably ranging from about 0.15 to about 1.5, more preferably from about 0.20 to about 1.2, even more preferably from about 0.4 to about 0.8, and most preferably from about 0.50 to about 0.60.

The positions on the saccharide units of the fructan alkylurethanes (I) where the said alkylcarbamate substituent or substituents are located, are not critical with respect to the present invention.

The fructan alkylurethanes (I) can be prepared in analogy with conventional methods for the preparation of urethanes of mono- and disaccharides, and of urethanes of polysaccharides such as starch. The products (I) can be prepared, for example, by reacting the substrate carbohydrate (levan or inulin) with the selected alkylisocyanate, in solution in a solvent which is inert with respect to the polysaccharide, the isocyanate and the reaction product. Suitable solvents include, for example, rather polar solvents or solvent mixtures, free of reactive hydroxyl and amine groups, such as dimethyl formamide and dimethyl sulfoxide.

Saturated alkylisocyanates can be prepared conventionally, e.g. by reacting a primary or secondary alkyl-amine with phosgene. Unsaturated alkylisocyanates can be prepared similarly from alkenyl-amines. Alpha-beta unsaturated alkylisocyanates of formula $R^2R^3$ C=CH—NCO (III) wherein $R^2$ represents hydrogen or an alkyl group and $R^3$ represents an alkyl or vinyl group, can be prepared by condensation of the aldehyde $R^2R^3$ C H—CHO with $Me_3$ C—NH2, followed by reaction of the resultant Schiff base (in equilibrium with its enamine form) with phosgene, and thermal elimination of $Me_3$ C—Cl, as disclosed by K. Koenig et al. (Angew. Chem., 91(4), 334–335 (1979)). Furthermore, various unsaturated alkylisocyanates are disclosed, inter alia in U.S. Pat. No. 3,890,383 and U.S. Pat. No. 3,803,062 of Dow Chemical Co.

The reaction between the fructan and the alkylisocyanate can be carried out, preferably in the absence of humidity, over a wide temperature range, typically from room temperature till the reflux temperature of the reaction mixture, preferably at a temperature from about 60° C. to about 80° C. The fructan is dissolved in a suitable solvent, where necessary under heating, and the isocyanate (optionally dissolved in the same or in another inert solvent which is preferably miscible with the former solvent) is then added to the dissolved fructan slowly and under stirring. The desired degree of substitution of the fructan alkylurethanes (I) can be obtained by controlling the ratio of the reactants. Since the reaction of an alkylisocyanate with an alcoholic hydroxyl group to form an urethane is virtually quantitative, the degree of substitution of the compounds (I) can be controlled by selection of the proper mole ratio of the alkylisocyanate per saccharide unit of the fructan substrate. Usually the reaction mixture is heated during a certain time with stirring in order to complete the reaction between the reagents. The reaction mixture can be worked up, for example, by precipitating the formed fructan alkylurethane (I) by pouring the reaction mixture in a precipitant solvent, i.e. a solvent which is miscible with the solvent or solvents used to dissolve the reagents but in which the fructan alkylurethane (I) is virtually not or poorly soluble.

A convenient method to synthesise a desired sucrose alkylurethane which is also suitable for the synthesis of fructan alkylurethanes (I) according to the present invention, has been described by W. Gerhardt, Abh. Dtsch. Akad. Wiss. Berlin, KL. Chem. Geol. Biol., Vol 1966(6), 24–36, (1967) (C.A., 68, 14323). It involves the transformation, in a one pot reaction, of sucrose with potassium cyanate and an alkyl halogenide, preferably an alkyl bromide, in dimethyl formamide.

Furthermore, the inventors have developed an alternative, very suitable method for the manufacture of fructan alkylurethanes (I), which enables to use as substrate, a fructan which may contain mono- and disaccharides to an extent of up to about 10% by weight. According to this process, the starting fructan, for example inulin containing about 8% mono- and disaccharides (such as e.g. RAFTILINE® ST from ORAFTI®, Belgium) or oligofructose containing about 5% mono- and disaccharides (such as e.g. RAFTILOSE® P95 from ORAFTI®, Belgium), are reacted in an inert solvent or solvent mixture (termed herein first solvent) with the alkylisocyanate which is optionally dissolved in the same or in another inert first solvent. After the reaction is completed, usually by heating under stirring for some time, the reaction mixture is treated, preferably after concentration by evaporation of a part of the first solvent under reduced pressure, with a solvent or solvent mixture (termed herein precipitant solvent) wherein the first solvent of the reaction as well as the alkylurethanes of the mono- and disaccharides remain in solution, but wherein the fructan alkylurethanes (I) are virtually not soluble. Accordingly, the formed fructan alkylurethanes (I) precipitate in the precipitant solvent from which they can be isolated easily by a conventional physical separation technique such as decantation and/or filtration, or centrifugation. To complete the removal of remaining first solvent and possibly present small amounts of alkylurethanes of mono- and disaccharides, the isolated reaction product can be washed and/or triturated with the precipitant solvent or with another suitable precipitant solvent, or other conventional techniques can be used such as e.g. redissolving and reprecipitation of the reaction product, followed by its isolation and drying.

Suitable first solvents include, for example, dimethyl formamide and dimethyl sulfoxide; suitable precipitant solvents include, for example, ethers, ketones, alcohols and esters.

The fructan alkylurethanes (I) are readily soluble at low concentration in water at room temperature and they present good to excellent tensio-active properties, even at very low concentration. Accordingly, they are very useful as surface-active agents because they significantly reduce interfacial tension between an aqueous liquid and a non-aqueous liquid, between an aqueous liquid and a solid, and between an aqueous liquid and a gas.

Preferably the fructan alkylurethanes (I) are used as surface-active agent in an aqueous medium, more preferably in water, at a concentration ranging from about 0.0005% to about 5%, preferably from about 0.001% to about 3%, more preferably from about 0.005% to about 2%, even more preferably from about 0.01% to about 1% (concentration in % weight/volume {% w/v}).

As a non-limiting illustration of the present invention, the preparation and tensio-active properties of some fructan alkylurethanes (I) are shown in the Examples and Tables below.

General Procedure used for the Manufacture of Fructan Alkylurethanes (I)

The reaction is preferably carried out in the absence of humidity with anhydrous reagents and solvents. The fructan, preferably conventionally dried, e.g. under vacuum over $P_2O_5$ or by azeotropically distilling off of the water by means of a suitable solvent, is dissolved, with stirring under heating, in a minimum amount of solvent, e.g. dimethyl formamide (DMF). To avoid thermal degradation, the temperature has to be kept below about 110° C. Preferably the mixture is kept between about 60° C. to about 80° C. until all fructan has dissolved. Then, at a temperature between about 60° C. to about 80° C., a pre-defined amount (determined in mole equivalents on fructose units in the fructan; for the calculation, the amount of fructan starting material is taken as composed of 100% fructose units) of a selected alkylisocyanate, optionally diluted with a suitable solvent, e.g. DMF, is added slowly, preferably dropwise, under vigorous stirring to the fructan solution and the obtained mixture is stirred at said temperature for a certain time to complete the reaction. After a few hours, the mixture may already turn cloudy by precipitation of formed fructan alkylurethane (I), but usually stirring is continued for about 24 hours in total after addition of the alkyl-isocyanate. Accordingly, the mixture is cooled to room temperature, optionally part of the solvent is removed by evaporation under reduced pressure, and a precipitant solvent, e.g. diethyl ether, is added under stirring. The formed fructan alkylurethane (I) precipitates, usually as a more or less sticky mass. After removal of the supernatant solvent, the sticky mass is repeatedly treated under stirring with solvent mixtures with decreasing polarity until the fructan alkylurethane (I) is obtained in powder or granulate form, which is then isolated and dried.

Alternatively, in order to avoid the formation of said sticky mass, the formed fructan alkylurethanes (I) can advantageously be isolated after completion of the reaction by slow, preferably dropwise, addition under vigorous stirring of the cooled and optionally concentrated reaction mixture to an excess of precipitant solvent, e.g. ether. Typically the formed fructan alkylurethanes (I) precipitate in a granular or powder form and can be easily isolated. After their separation from the solvent mixture, e.g. by filtration, the fructan alkylurethanes (I) can be further purified by washing, trituration with a non-solvent, e.g. ether, or they may be redissolved and reprecipitated to remove possibly included solvent and impurities.

The formation of the fructan alkylurethanes (I) has been confirmed by IR- spectroscopy {presence of —NH—CO— band at 1705 $cm^{-1}$ (amide I band) and 1543 $cm^{-1}$ (amide II band)} and by $^{13}C$-NMR spectroscopy (where following resonance peaks were found for inulin N-n-octylcarbamate: $\partial${ppm; 68 MHz}: 13.87; 22.05; 26.23; 28.64; 29.33; 30.74; 31.21; 35.77; 61.45; 73.99; 76.56; 81.59; 103.19 and 156.08).

As to the synthesis of inulin alkylcarbamates (I), the yields commonly obtained are good. For the synthesis made at a 0.2 mole scale, typical yields of inulin octylcarbamates (DS: 0.52–0.59) obtained are as follows:

with RAFTILINE® HP (inulin with ($\overline{DP}$) of about 25): yield about 70–95% with RAFTILINE® ST (inulin with ($\overline{DP}$) of about 10): yield about 55–75% with RAFTILOSE® P95 (95% w/w oligofructose with ($\overline{DP}$) from 2 to 7): yield about 50–65%.

The above general procedure is further illustrated by the following examples. The tensio-active properties of the fructan alkylurethanes (I) were determined by measuring the surface tension at 20° C. of an aqueous solution of the compounds with a tensiometer following the Wilhelmy or the Du Nouy Ring method.

EXAMPLE 1

Inulin N-n-octylcarbamate (1)

In a 100 ml flask, 5.0 g inulin (RAFTILINE® HP with a ($\overline{DP}$) of about 25; 27.7 millimole fructose equivalents) were dissolved under stirring at about 70° C. in 8 ml dry DMF. To the yellowish solution 2.9 ml n-octylisocyanate (16.7 millimole; 0.6 mole equivalents determined on fructose units) were added dropwise with stirring at 70° C. Stirring was continued for 24 hours at 70° C. Then, after cooling, most of the DMF was evaporated under reduced pressure (±6.7 Pa; 0.05 mm Hg). To the residue at room temperature, 10 ml of dry diethyl ether was added under stirring and the mixture was stirred for 1 hour. The white precipitate formed was isolated by filtration, washed with 15 ml dry ether and the residual solvents (DMF and ether) were removed under reduced pressure (±6.7 Pa; 0.05 mm Hg), yielding inulin N-n-octyl-carbamate (1) with a degree of substitution (DS) of 0.56 (determined by $^1H$-NMR—270 MHz). Compound (1) was obtained as a white powder in a yield of 92%. The efficiency calculated as [DS/(molar ratio octylisocyanate/fructose equivalent)] was 93%. The surface tension of product (1) in a 0.01% w/v solution in water was 32.4 mN/m.

EXAMPLE 2

Inulin N-n-octylcarbamate (2)

In a 500 ml flask, 33.3 g inulin (RAFTILINE® HP with a ($\overline{DP}$) of about 25; 0.185 mole fructose equivalents) was dissolved at 60° C. in 60 ml dry DMF. To the yellowish solution kept at 60° C., 19.56 ml n-octylisocyanate (0.111 mole; 0.6 equivalents determined on fructose units) was added dropwise under stirring. Then the mixture was heated to 70° C. and stirred for 24 hours. After cooling to room temperature, 150 ml diethyl ether was added slowly under vigorous stirring. After stopping the stirring, the reaction product quickly settled and most of the solvent was removed by decantation. Under stirring 100 ml dry ether was added to the residue, which became gummy-like. After addition of another 50 ml ether the residue started to granulate and after 1 hour stirring a white suspension was formed. The precipitated solid was filtered off, washed with dry ether and dried under reduced pressure (±6.7 Pa; 0.05 mm Hg), yielding inulin N-n-octylcarbamate (2) with a degree of substitution (DS) of 0.58 (determined by $^1$H-NMR—270 MHz) in a yield of about 95% and with an efficiency of 96%. The surface tension of product (2) in a 0.01% w/v solution in water was 34 mN/m.

Several other inulin alkylurethanes (I) have been prepared by reacting various grades of inulin with various n-alkylisocyanates in accordance with the general procedure described above, and their tensio-active properties were determined. These products and data, including also Examples 1 and 2 above, are listed in Table 1 below.

TABLE 1

Inulin N-n-alkylcarbamates (I)

| Product No | inulin grade* ($\overline{DP}$) | alkyl group** | degree substit. (DS)° | Surface tension at 0.01% w/v in water (mN/m)# |
|---|---|---|---|---|
| 1 | 25 | n-octyl | 0.56 | 32.4 |
| 2 | 25 | n-octyl | 0.58 | 34 |
| 3 | 25 | n-propyl | 0.13 | 61.6 |
| 4 | 25 | n-propyl | 0.18 | 65.2 |
| 5 | 25 | n-propyl | 0.35 | 59.2 |
| 6 | 25 | n-propyl | 0.72 | 46 |
| 7 | 25 | n-propyl | 1.2 | 41.2 |
| 8 | 25 | n-hexyl | 0.37 | 44 |
| 9 | 25 | n-hexyl | 0.46 | 36 |
| 10 | 25 | n-octyl | 0.21 | 50.8 |
| 11 | 25 | n-octyl | 0.37 | 45.6 |
| 12 | 25 | n-octyl | 0.55 | 38.5 |
| 13 | 25 | n-octyl | 0.56 | 32.4 |
| 14 | 25 | n-octyl | 0.78 | 36 |
| 15 | 25 | n-octyl | 0.86 | 36.8 |
| 16 | 25 | n-dodecyl | 0.21 | 42 |
| 17 | 25 | n-dodecyl | 0.29 | 31.6 |
| 18 | 25 | n-octyl | 0.56 | 35.2 |
| 19 | 25 | n-octyl | 0.59 | 35.6 |
| 20 | 10 | n-octyl | 0.53 | 34.6 |
| 21 | 95% DP2-7 | n-octyl | 0.51 | 31.7 |
| 22 | 25 | n-octyl | 0.56 | 35 |
| 23 | 25 | n-dodecyl | 0.34 | 56 |
| 24 | 25 | n-octadecyl | <0.05°° | 63.5 |

*The inulin grades used were: ($\overline{DP}$: 25) = RAFTILINE ® HP; ($\overline{DP}$: 10) = RAFTILINE ® ST and (95% DP 2-7) = RAFTILOSE ® P95.
**The isocyanates were commercially available technical grade products.
°DS: measured by $^1$H-NMR - 270 MHz
°°not measured by NMR; value estimated based on 0.05 mole equivalent C18 alkyl isocyanate put into reaction.
The value of the surface tension of pure water measured under the same conditions ranges between about 72 to 74 mN/m.

Furthermore, for some of the inulin N-n-octylcarbamates (I), the critical micelle concentration (CMC) has been determined which are shown in FIG. 1, FIG. 2 and FIG. 3.

BRIEF DESCRIPTION OF THE DRAWINGS

FIG. 1: presents the surface tension in function of the concentration of inulin ($\overline{DP}$: 25) N-n-octylcarbamate (DS: 0.56) (18) measured at room temperature in water and the resulting critical micelle concentration (CMC=12.8 $10^{-3}$ g/l);

FIG. 2: presents the surface tension in function of the concentration of inulin ($\overline{DP}$: 10) N-n-octylcarbamate (DS: 0.53) (20) measured at room temperature in water and the resulting critical micelle concentration (CMC=16.0 $10^{-3}$ g/l);

FIG. 3: presents the surface tension in function of the concentration of inulin (95% DP: 2-7) N-n-octylcarbamate (DS: 0.51) (21) measured at room temperature in water and the resulting critical micelle concentration (CMC=23.9 $10^{-3}$ g/l).

The experimental data shown in Table 1 and in FIGS. 1 to 3 clearly indicate that the alkylurethanes (I) present useful to excellent tensio-active properties at low concentration e.g. a concentration of 0.01% w/v in water and even at a concentration of 0.001% w/v in water, and from said data it can be concluded that the alkylurethanes (I) have great potential as surfactants.

EXAMPLE 3

Biodegradability

The alkylurethanes (I) are well biodegradable. To illustrate said characteristic, the Biological Oxygen Demand (BOD) and Chemical Oxygen Demand (COD) for some inulin N-n-octylalkylcarbamates, measured by the Sapromat method, are given below:

| Carbamate (I) Product No. | BOD (mg $O_2$/g) | COD (mg $O_2$/g) | BOD/COD |
|---|---|---|---|
| 18 | 620 | 1064 | 0.583 |
| 21 | 943 | 1108 | 0.851 |

EXAMPLE 4

Foaming Properties

The alkylcarbamates (I) are good foaming agents and present good foam stabilising effects. To illustrate these properties, results of measurements by means of a gas injection method are presented in Table 2 below.

The gas injection method used was as follows. Foam was made in a reproducible manner by blowing a defined volume of nitrogen gas at a constant flow rate through a sintered glass disc at the bottom of a cylindrical glass tube containing a known volume of the solution to be foamed. After providing a defined amount of gas (exactly 100 cm³), the evolution of the liquid phase and the foam phase were determined as a function of time. All glass material used was placed in chromic acid overnight and thoroughly rinsed with milli-Q water before use. The experimental conditions were as follows: room temperature; gas flow: 100 cm³ (5l/h for exactly 72 seconds); disc porosity diameter: 16–24 micrometer; column size: 0.4 m×0.030 m (inner diameter); sample volume: 20 ml; duration of the analysis: 20 minutes with measurement of the foam height every minute, and samples of the carbamates were dissolved at 0.1% (1000 ppm) in milli-Q water. The foam height as a function of time was measured and expressed in MD value's, i.e. the foam volume/liquid volume. The results are summarised in Table 2.

TABLE 2

Foaming properties of inulin N-n-octylcarbamates (I)

| Product No | inulin grade* | Degree substit.° | MD initial | MD 3 min | MD 7 min | MD 15 min | MD 20 min |
|---|---|---|---|---|---|---|---|
| 19 | ($\overline{DP}$: 25) | 0.59 | 53.6 | 14.1 | 11.0 | 9.6 | 9.1 |
| 20 | ($\overline{DP}$: 10) | 0.53 | 36.0 | 10.8 | 9.4 | 7.9 | 7.4 |
| 21 | 95% DP2-7 | 0.51 | 36.9 | 11.7 | 9.4 | 7.9 | 7.4 |

*The inulin grades used were: ($\overline{DP}$: 25) = RAFTILINE ® HP; ($\overline{DP}$: 10) = RAFTILINE ® ST and (95% DP 2-7) = RAFTILOSE ® P95.
°DS measured by $^1$H-NMR - 270 MHz The data of Table 2 clearly indicate the potential of inulin N-n-alkyl-carbamates (I) as foaming agents and as foam stabilisers.

EXAMPLE 5

Interfacial Tension

The interfacial tension has been measured by means of the Du Nouy ring method at 20° C. for water/oil systems in which inulin N-n-alkylcarbamates (I) were used as surface-active agent. The results are presented in Table 3. The products (1) (Product No) are described in Table 1.

TABLE 3

Interfacial tension of inulin N-n-alkyl carbamates (I)

| Surfactant (I) | | | Interfacial |
|---|---|---|---|
| Product No | Conc. in % w/v in surfactant (water) solution | Type of oil | Tension at 20° C. (mN/m) |
| 22 | 0.1 | paraffinic oil* | 5 |
| 22 | 0.01 | paraffinic oil* | 7 |
| 22 | 0# | paraffinic oil* | 44 |
| 22 | 0.1 | aromatic oil** | 2.7 |
| 22 | 0.01 | aromatic oil** | 5.4 |
| 22 | 0# | aromatic oil** | 29 |
| 22 | 0.1 | silicon oil*** | 5.6 |
| 22 | 0.01 | silicon oil*** | 13.4 |
| 22 | 0# | silicon oil*** | 29.5 |
| 22 | 0.1 | vegetable oil**** | 3 |
| 22 | 0.01 | vegetable oil**** | 4.8 |
| 22 | 0# | vegetable oil**** | 12.6 |
| 23 | 0.01 | paraffinic oil* | 20 |
| 24 | 0.01 | paraffinic oil* | 27 | comparative test
*Isoparaffinic hydrocarbon "Isopar M" (Exxon)
**naphthalenic oil "Solvesso 200" (Exxon)
***silicon oil "Cyclomethicon E344" (Dow)
****soybean oil (Sainor)

EXAMPLE 6

Emulsifying Properties of Alkylurethanes (I)

The alkylurethanes (I) present very good emulsifying properties, in particular with respect to oil/water systems. Typical oils include, for example, vegetable oils, hydrocarbon oils and mineral oils, and any mixture therefore. The emulsions may find wide applications, depending of the nature of the oil, in various fields, such as, for example, in household products, in person care applications, in agrochemicals, in pesticides and in industrially used emulsions.

The oil content in the emulsions can, for example, range from about 5 wt % to about 75 wt %. The total concentration of the surfactant, alkylcarbamate (I) or a mixture of two or more alkylcarbamates (I), in the surfactant solution used to build the water phase can, for example, range from about 0.3 wt % to about 3 wt %, typically from about 0.5 wt % to about 2 wt %.

The emulsifying properties of the alkylurethanes (I) are illustrated by the example below in which various oil/water emulsions, containing one or more alkylcarbamates (I) as surfactant, were prepared and evaluated according to standard procedures.

Preparation of the Emulsions

To 25 ml surfactant solution, composed of a given concentration (wt %) of one or more alkylcarbamates (I) in demineralised water, were added dropwise 25 ml oil, while the mixture was stirred by means of an Ultra-Turrax* (CAT X620) (*trade name). The oil was added during the first step of a four step mixing process, in which the mixing speed was stepwise increased as indicated in table 4 below, yielding the emulsion. However, the mixing procedure is not critical since also other procedures than the one given yield about the same results.

TABLE 4

| | Mixing procedure | | | |
|---|---|---|---|---|
| Step | 1 | 2 | 3 | 4 |
| Stirring speed (rpm) | 9,500 | 13,500 | 20,500 | 24,000 |
| Stirring time (sec) | 120 | 60 | 45 | 30 |

Evaluation of the Emulsions

The evolution in time of the emulsions kept at room temperature was followed both microscopically (evolution of the droplet size) and macroscopically (visual check for oil/water separation). The results are shown in Table 5 below.

TABLE 5

Evaluation of oil/water emulsions containing alkylcarbamates (I)

| Total wt % of surfactants (I) in the surfactant solution (= water phase)* | Alkylcarbamate (I) Product No** | Oil | Stability of emulsion (days) (2) |
|---|---|---|---|
| 0.5 | 22 | isoparaffinic oil (1) | >90 |
| 2 | 22 | isoparaffinic oil (1) | >90 |
| 1 | 22 | soybean oil | >20 |
| 1 | 24 | isoparaffinic oil (1) | >10 |
| 1 | 23 | isoparaffinic oil (1) | >30 |
| 1 | 22 + 23 | isoparaffinic oil (1) | >10 |
| 1 | 22 + 24 | isoparaffinic oil (1) | >10 |
| 1 | 23 + 24 | isoparaffinic oil (1) | >10 |
| 1 | 22 + 23 + 24 | isoparaffinic oil (1) | >10 |

*In the mixture of alkylcarbamates (I), the products (I) were used at the same weight %, i.e. respectively in the weight ratio 1:1 and 1:1:1.
**The product corresponding to the product number is described in Table 1.
(1) isoparaffinic hydrocarbon "Isopar M" (trade name of Exxon)
(2) the emulsion was stable (no oil/water separation observed) for at least the indicated time.

EXAMPLE 7

Emulsions Containing Alkylcarbamates (I) and Inulin

The stability of oil/water emulsions containing one or more alkylcarbamates (I) as surfactant can be further improved by increasing the viscosity of the aqueous phase by the addition of inulin to it. In typical test runs, respectively 0.5 g; 1 g; 2 g and 2.5 g inulin (RAFTILINE® ST or RAFTILINE® HP) (all of about 96 wt % dry matter) were slowly added to 25 ml surfactant solution composed of 1 wt %, respectively 0.5 wt%, alkylcarbamate No 22 in demineralised water under stirring (Ultra-Turrax at 8,000 rpm for 15 to 60 sec). With the so obtained surfactant solution, emulsions with isoparaffinic hydrocarbon oil ("Isopar M"; trade name of Exxon) were prepared according to the procedure described in Example 6. All the emulsions obtained were still stable (visual inspection) after storage for 20 days at room temperature.

EXAMPLE 8

Use of Alkylurethanes (I) as Dispersants

Dispersions were made from surfactant solutions containing one or more alkylcarbamates (I) described above by adding a product in powder form to said surfactant solution under stirring by means of an Ultra-Turrax*(CATx620) (*trade name). The powder was added during the first step of a four step mixing process (1st step: 9,500 rpm; 90 sec.; 2nd step: 13,500 rpm; 60 sec.; 3rd step: 20,500 rpm; 30 sec.; 4th step: 24,000 rpm; 15 sec.). However, the mixing procedure is not critical since also other procedures than the one given above yield about the same results. The dispersions obtained were inspected visually and microscopically (100×) in function of the time.

Test runs, for example a dispersion of 0.5 g carbon black (Efltex 575 variant, Cabot Corporation) in 25 ml surfactant solution of 0.5 wt % alkylcarbamate No 22, showed that with alkylcarbamates (I) as surfactants, dispersions with a very good stability were obtained in which the particle size of the dispersed product was smaller than in a corresponding dispersion similarly made from water (without any surfactant) and the powder product. The above indicates that alkylcarbamates (I) have great potential as dispersants, particularly for hydrophobic products, since they enable to prepare dispersions with good stability.

The above indicated properties of the alkylcarbamates (I) and the combination thereof in the individual alkylcarbamates, make that the fructan alkylurethanes (I) are highly valuable for use as surface-active agents in various compositions and in premixes for the preparation of said compositions. These compositions and premixes can be prepared according to conventional techniques, for example, by simple mixing, preferably under low speed stirring, of all ingredients of the composition in the required amounts, including the selected one or more alkylurethanes (I), or by addition of a desired amount of the one or more selected alkylurethanes (I) to a pre-mix of all other ingredients, or by adding a pre-mix containing all required ingredients, including the selected one or more alkylurethanes (I), to a medium such as water or an aqueous or non-aqueous liquid, for example an oil, or a pasty composition.

The surface-active agents of the present invention are suitable for use as detergents, emulsifiers, emulsion stabilisers, liposome stabilisers, foaming agents, foam stabilisers and/or wetting agents in various household and industrial applications, such as for example in detergents for laundry washing, detergents for dish washing, industrial detergents, emulsifiers in cosmetics, emulsifiers and stabilisers in inks, in paintings and in coating compositions, and foaming agents and/or foam stabilisers in shampoo's.

Furthermore, the alkylurethanes (I) present good thermal and chemical stability in combination with good biodegradability and they are free of phosphor/phosphates. Furthermore, the main raw materials for the manufacture of the alkylcarbamates (I), i.e. the fructans levan and inulin, are commonly agro-chemicals, i.e. carbohydrates from vegetal origin which in fact constitute renewable resources. The combination of said features makes that the fructan N-alkylcarbamates (I) are environmentally well acceptable. Besides, said carbohydrates, particularly inulin, are available at industrial scale in suitable quality and at acceptable raw material prices which is an economically very important feature, making the use of alkylurethanes (I) as surfactants at industrial scale possible and attractive.

What is claimed is:

1. A fructan N-alkylurethane which is composed of saccharide units of general formula:

$$A(O-CO-NH-R)_s$$

wherein

A represents a fructosyl unit (F) or a terminal glucosyl unit (G) of said fructan, being a levan or an inulin, with a degree of polymerization (DP) of minimum 3, (O—CO—NH—R) represents an N-alkylaminocarbonyloxy group replacing a hydroxyl group of the saccharide unit A, wherein R represents a linear or branched, saturated or unsaturated alkyl group containing from 3 to 22 carbon atoms and any mixture thereof, and s represents the number of N-alkylaminocarbonyloxy groups per saccharide unit which is expressed as degree of substitution (DS), and said DS has a value ranging from 0.10 to 2.0.

2. A fructan N-alkylurethane according to claim 1, wherein the alkyl group R is a saturated $C_3$–$C_{22}$ alkyl group or a mixture of said alkyl groups.

3. A fructan N-alkylurethane according to claim 1, wherein the alkyl group R is a mono-unsaturated $C_3$–$C_{22}$ alkyl group or a mixture of said unsaturated alkyl groups.

4. A fructan N-alkylurethane according to claim 1, wherein the alkyl group R is a linear or branched $C_6$–$C_{18}$ alkyl group or a mixture thereof.

5. A fructan N-alkylurethane according to claim 1, wherein the degree of substitution (DS) has a value ranging from 0.15 to 1.5.

6. A fructan N-alkylurethane according to claim 1, wherein the fructan is an inulin.

7. A fructan N-alkylurethane according to claim 6, wherein the inulin has an average degree of polymerization ($\overline{DP}$) ranging from 3 to 100.

8. A fructan N-alkylurethane according to claim 6, wherein the inulin is an oligofructose with a DP<10.

9. A fructan N-alkylurethane according to claim 1, wherein the fructan is a polydisperse linear or slightly branched inulin or a mixture thereof with a degree of polymerization (DP) ranging from 3 to 100.

10. A fructan N-alkylurethane according to claim 1, which is selected from the group consisting of inulin N-n-octylcarbamate, inulin N-n-dodecylcarbamate and inulin N-n-octadecylcarbamate.

11. Process for the manufacture of a fructan N-alkylurethane claimed in claim 1, comprising reacting a fructan dissolved in a first solvent with such an amount of alkylisocyanate that an N-alkylurethane is yielded having a degree of substitution (DS) ranging from 0.10 to 2.0, the first solvent being inert with respect to the fructan, the isocyanate and the alkylurethane, followed by precipitation of the formed alkylurethane, optionally after partial removal of the first solvent by evaporation under reduced pressure, either by addition under stirring of a precipitant solvent to the reaction mixture or by slowly pouring under stirring the reaction mixture into a precipitant solvent, followed by isolation of the precipitated alklyurethane.

* * * * *